US010167159B2

(12) United States Patent
Ingole et al.

(10) Patent No.: US 10,167,159 B2
(45) Date of Patent: Jan. 1, 2019

(54) APPARATUS AND METHODS FOR TRANSPORTING WEBS OF MATERIAL

(71) Applicant: CURT G. JOA, INC., Sheboygan Falls, WI (US)

(72) Inventors: Sudeep Ingole, Sheboygan, WI (US); Gottfried Jason Hohm, Sheboygan Falls, WI (US); Debra Heus Bowe, Kiel, WI (US); Thomas Muhs, Kiel, WI (US); Jeffrey A. Middlesworth, Sheboygan, WI (US); Robert E. Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 15/661,408

(22) Filed: Jul. 27, 2017

(65) Prior Publication Data

US 2017/0320693 A1 Nov. 9, 2017

Related U.S. Application Data

(62) Division of application No. 14/737,306, filed on Jun. 11, 2015.

(Continued)

(51) Int. Cl.
*B65H 27/00* (2006.01)
*B65H 20/06* (2006.01)
(Continued)

(52) U.S. Cl.
CPC .............. *B65H 27/00* (2013.01); *B65H 20/06* (2013.01); *B65H 20/10* (2013.01);
(Continued)

(58) Field of Classification Search
CPC . B65H 3/10; B65H 3/12; B65H 3/124; B65H 5/22; B65H 5/222; B65H 5/224;
(Continued)

(56) References Cited

U.S. PATENT DOCUMENTS 4,136,591 A 1/1979 Helm et al.
6,023,908 A 2/2000 Vetsch
(Continued)

FOREIGN PATENT DOCUMENTS

DE 1611768 A1 1/1971
DE 2435991 A1 4/1975
(Continued)

OTHER PUBLICATIONS

International Search Report from PCT/US15/35409, dated Sep. 16, 2015, 8 pages.
(Continued)

*Primary Examiner* — Michael C McCullough
(74) *Attorney, Agent, or Firm* — Ryan Kromholz & Manion, S.C.

(57) ABSTRACT

Methods and apparatus for transporting either an entire web or discrete components of disposable products such as diaper components down the machine using mechanical forces to grip the nonwoven web and transfer it from one belt or roll to another without or reducing added vacuum. There is a carrier nonwoven web that goes down the length of the machine and other substrates are added on top of this layer, and the machine provides sufficient gripping to allow transport of diaper components through the fabrication process. Securing and releasing forces are supplied so that the components can be retained at some points and released at others.

7 Claims, 7 Drawing Sheets

Related U.S. Application Data (60) Provisional application No. 62/010,773, filed on Jun. 11, 2014.

(51) Int. Cl.
  *B65H 20/10* (2006.01)
  *A61F 13/15* (2006.01)

(52) U.S. Cl.
  CPC .. *A61F 13/15577* (2013.01); *B65H 2404/531* (2013.01); *B65H 2406/332* (2013.01); *B65H 2406/3662* (2013.01); *B65H 2801/57* (2013.01)

(58) Field of Classification Search
  CPC .......... B65H 5/226; B65H 2301/44735; B65H 2404/1363; B65H 2406/30; B65H 2406/312; B65H 2406/3122; B65H 2406/3124; B65H 2406/32; B65H 2406/36; B65H 2406/366; B65H 2406/3662; B65H 2406/36625; B65H 2406/3612; B65H 2406/3614
  See application file for complete search history.

(56) References Cited

U.S. PATENT DOCUMENTS

| | | |
|---|---|---|
| 6,705,499 B1 | 3/2004 | Ruckmann et al. |
| 7,065,948 B2 | 6/2006 | Kranich |
| 7,094,373 B2 | 8/2006 | Heyn et al. |
| 2003/0018313 A1 | 1/2003 | Tanzer et al. |
| 2003/0062120 A1 | 4/2003 | Lehner et al. |
| 2009/0051747 A1* | 2/2009 | Okada .................... B41J 13/226 347/104 |
| 2012/0157287 A1 | 6/2012 | Yamamoto |
| 2017/0327330 A1* | 11/2017 | Aoki ........................ B65H 3/48 |

FOREIGN PATENT DOCUMENTS

| | | | |
|---|---|---|---|
| EP | 2221414 A1 | 8/2010 | |
| EP | 2385007 A2 | 11/2011 | |
| EP | 3020666 A1 * | 5/2016 | ............ B65H 29/56 |
| GB | 191302662 | 12/1913 | |
| GB | 191302662 A | 12/1913 | |
| GB | 2127382 B | 4/1984 | |
| GB | 2127382 | 1/1987 | |
| JP | H03118914 U | 12/1991 | |
| JP | H03118915 U | 12/1991 | |
| JP | H03118954 U | 12/1991 | |
| JP | 1997131364 A | 5/1997 | |
| JP | 2002370416 A | 12/2002 | |
| JP | 4005575 B2 | 11/2007 | |
| WO | WO 2011/091843 A1 | 8/2011 | |

OTHER PUBLICATIONS

Webpage, "Venturi effect", https://en.wikipedia.org/wiki/Venturi_effect, 4 pages, dated Aug. 13, 2015.

Webpage, drawing, https://en.wikipedia.org/wiki/Venturi_effect#/media/File:Venturifixed2.PNG, 1 page, dated Aug. 13, 2015.

Supplementary European Search Report elating to EP15806606, dated Jun. 20, 2018, 11 pages.

\* cited by examiner

APPARATUS AND METHODS FOR TRANSPORTING WEBS OF MATERIAL

RELATED APPLICATIONS

This application is a division of co-pending U.S. patent application Ser. No. 14/737,306, filed 11 Jun. 2015, which claims the benefit of U.S. Provisional Patent Application Ser. No. 62/010,773, filed 11 Jun. 2014.

BACKGROUND OF THE INVENTION

This invention relates to a method and apparatus for rapidly and accurately transporting a discrete article or a web of material. This invention is not limited to its preferred use, carrying components of a disposable diaper or sheet of paper; but instead the methods and apparatus' of the present invention may be used in wide ranging applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in co-pending U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed.

A sealer bonds the webs at appropriate locations prior to individual diapers being cut from the folded and sealed webs.

Roll-fed web processes typically use splicers and accumulators to assist in providing continuous webs during web processing operations. A first web is fed from a supply wheel (the expiring roll) into the manufacturing process. As the material from the expiring roll is depleted, it is necessary to splice the leading edge of a second web from a standby roll to the first web on the expiring roll in a manner that will not cause interruption of the web supply to a web consuming or utilizing device.

In a splicing system, a web accumulation dancer system may be employed, in which an accumulator collects a substantial length of the first web. By using an accumulator, the material being fed into the process can continue, yet the trailing end of the material can be stopped or slowed for a short time interval so that it can be spliced to leading edge of the new supply roll. The leading portion of the expiring roll remains supplied continuously to the web-utilizing device. The accumulator continues to feed the web utilization process while the expiring roll is stopped and the new web on a standby roll can be spliced to the end of the expiring roll.

In this manner, the device has a constant web supply being paid out from the accumulator, while the stopped web material in the accumulator can be spliced to the standby roll.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the: left side of the product. In this manner, for a single product, one of the two ears will have been rotated 180°.

Continual improvements and competitive pressures have incrementally increased the operational speeds of disposable diaper converters. As speeds increased, the mechanical integrity and operational capabilities of the applicators had to be improved accordingly.

One such sought improvement is to minimize reliance on vacuum conveyors to transport either continuous webs of material or discrete components of disposable products. The current process uses high vacuum levels and a lot of air flow to hold the substrate to the belt or transporting pucks. This process holds and transfers sufficiently, but has high cost to acquire this vacuum and high cost for noise abatement.

SUMMARY OF THE INVENTION

Provided are methods and apparatus for transporting either an entire web or discrete components of disposable products. The invention is a means of conveying the web or diaper components down the machine using mechanical forces to grip the nonwoven web and transfer it from one belt or roll to another without or reducing added vacuum. There is a carrier nonwoven web that goes down the length of the machine and other substrates are added on top of this. Methods and apparatus are disclosed to provide sufficient gripping to allow transport of diaper components through the fabrication process. Securing and releasing forces are supplied so that the components can be retained at some points and released at others.

Clamping of components or webs is disclosed where it may only be necessary to grip portions of the nonwoven perhaps on the edges, or what would ultimately be the four corners of the diaper. This can be done with clamps affixed to conveying belts gripping the corners. It can also be done with tabs penetrating slots cut into a nonwoven early in the process. These tabs can be affixed to the belts or on transfer rolls.

Also disclosed is a method of preworking the nonwoven with intermeshing gears so that the nonwoven takes on a texture, and has more 3D loft so that the switchable surface described below can grip it more readily. The nonwoven can also be preheated to soften it and make it easier for gripping with smooth as well as rough surfaces.

In another embodiment, a switchable surface is disclosed. In this embodiment, a surface grips a nonwoven from below, but can be switched off so that the surface does not grip the non-woven during periods of desired transport of the non-woven to another belt or roller.

A system according to an embodiment of the present invention includes a conveyor comprising a material surface for moving a web material along a transfer path, wherein the material surface sufficiently frictionally engages the web material to convey the material along the transfer path without using a vacuum drawn through the material surface. The web material may be nonwoven web material, and the material surface may include a sand texture, hook material from a hook-and-loop fastener arrangement, and/or a plurality of spikes protruding from the material surface.

According to another embodiment of a system according to the present invention, it may include a conveyor comprising a material surface for moving a web material along a transfer path and a plurality of holes formed through the material surface, the plurality of holes in fluid communication with a cavity. A fan may be included for drawing air out of the cavity to cause air to flow through the holes and into the cavity. Preferably, the fan is driven by the conveyor.

An embodiment of a method according to the present invention includes the step of frictionally conveying a web material along a transfer path. Additionally or alternatively, a passive Venturi draw may be created whereby the conveyor drives a fan to cause a web material to hold to a material surface for conveyance.

BRIEF DESCRIPTION OF THE DRAWINGS

FIGS. 1-6 generally represent a prior art apparatus and method of conveying and handing off articles by providing high speed vacuum porting to selected vacuum pattern areas on a rotating cylindrical roll.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

FIGS. 1-6 generally describe a rotating anvil using vacuum to hold discrete pieces on a moving web, in the prior art. High speed vacuum is also used in a similar manner to transport discrete pieces and entire webs on flat conveyors through the manufacturing process. The present invention relates to transporting discrete pieces and entire webs through both rotation and flat conveyance by minimizing the vacuum usage shown in FIGS. 1-6 and on prior art flat vacuum conveyors (not shown).

Figure 1:
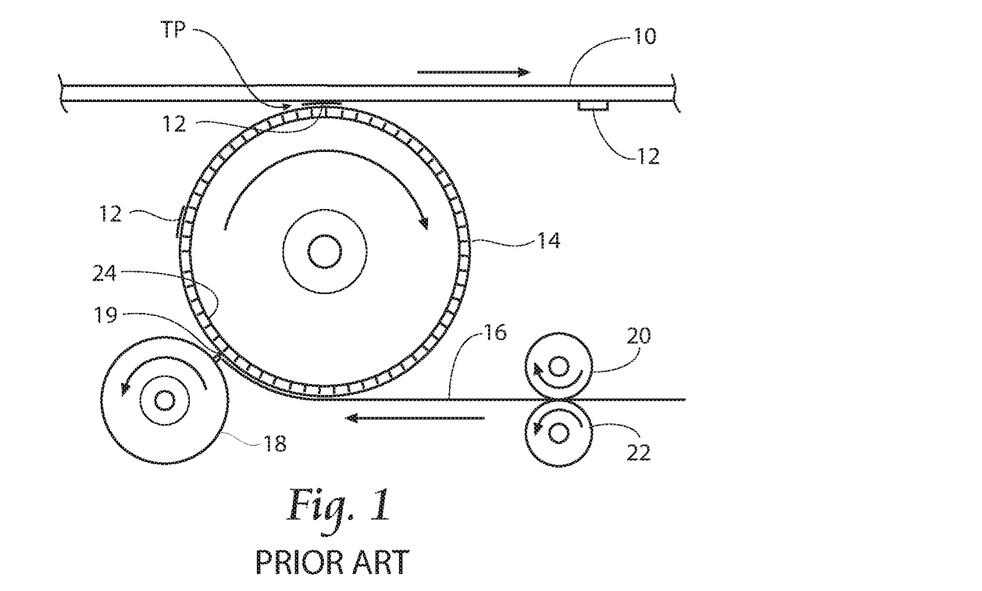
FIG. 1 is a diagrammatic side view of a prior art process.

Referring to the drawings there is seen in FIG. 1 a diagrammatic illustration of a prior art process for applying tabs to webs in a diaper making process. This prior art method of affixing the segments 12 to the web 10, with a different anvil, the new anvil 114 described below. Web 10 is a composite material used in formation of diapers which is generally formed of various layers of material such as plastic back sheets, absorbent pads and nonwoven topsheets. A series of ears 12 are applied to web 10. In the illustrated process a rotatable vacuum anvil 14 is used to supply the ears 12 to web 10. Anvil 14 has internally reduced air pressure or vacuum (not shown), and a plurality of openings 24 are provided through its surface to enable suction of the tab segments 12 against the anvil surface 14. A web of the ear tab forming material 16 is fed by rollers 20 and 22 against the anvil surface 14 where it is cut into segments by a rotary knife 18.

In the prior art, the surface of the anvil roll 14 has vacuum holes 24 on its smooth surface. In a typical configuration of a slip-and-cut applicator, there is a pattern of vacuum holes 24 distributed to evenly draw the entering web onto the surface of anvil 14 and thence into the cut point where the knife edge 18 engages the anvil 14.

It can be seen from FIG. 1 that in the prior art, the infeed of the ear tab forming material 16 can be at a first speed (with individual ears 12 spaced together), after which the individual ears gain speed to the speed of the anvil 14. Typical infeed speeds could be 120 mm/product for the infeed, while anvil speeds could be 450 mm/product on the anvil. This transition from the slower first speed to the quicker second speed takes place at the cut point, the ear tab forming material 16 slipping on the anvil 14 until cut. However, immediately at the transition cut point 18 from the slower speed to the faster speed, it is desired to place vacuum on the ears because centrifugal force would try to throw the ears off of the vacuum anvil 14.

Figure 2:
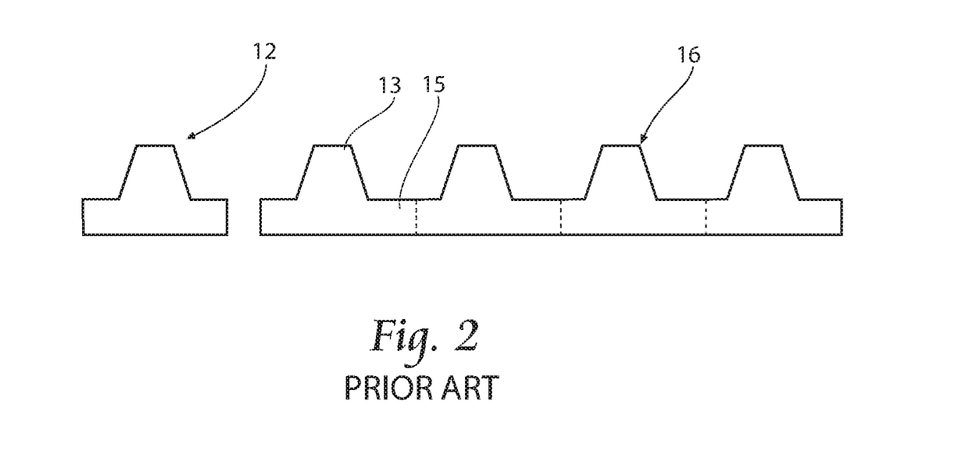
FIG. 2 is a top view of a prior art ear forming web including an individual ear detached from the web.

A continuous ear forming web 16 is provided to the system. The web 16 is comprised of two portions, 12a and 12b, as shown in FIG. 2. Segment 12a is more specifically referred to as the tab section of the ear 12, segment 12b is the ribbon section of the ear 12. The ear forming material 16 is cut into individual ears 12 by the rotary knife 18 as shown in FIG. 1, along lines such as the dashed lines shown in FIG. 2.

Figure 3:
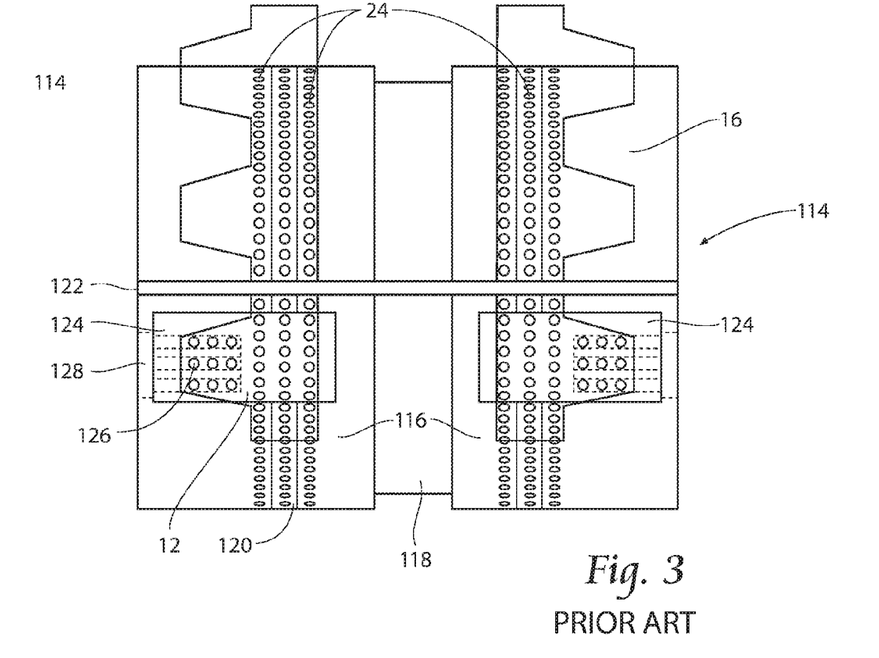
FIG. 3 is a front view of a prior art anvil roll.

Referring now to FIG. 3, a front view of an anvil roll 114 of the prior art is shown carrying ear forming material 16 (and later, an ear 12) in phantom. The anvil roll 114 is preferably formed with two vacuum portions 116 separated by a center groove portion 118. The vacuum portions 116 are preferably mirror images of each other. The anvil roll 114 is symmetrical about a center plane through its circumference. Each vacuum portion 116 contains several circumferential rows of circular vacuum holes 24. Each vacuum portion 116 may also contain a circumferential groove 120 with an additional circumferential row of vacuum holes 24 located in the circumferential groove 120.

The preferred embodiment of the anvil roll 114 of the prior art is also formed with two diametrically opposed anvil pockets 122 and two diametrically opposed pairs of ear retaining portions 124. The ear retaining portions can be created as inserts, with different vacuum patterns applied as the user deems necessary. Each anvil pocket 122 is a groove which extends across the face of the entire anvil roll 114. One ear retaining portion 124 is located on each of the vacuum portions 116. Each ear retaining portion 124 has an ear vacuum hole pattern 126 made of a plurality of vacuum holes 24 located at or near the surface of the anvil roll 144. The preferred embodiment, as shown in FIG. 3 is a plurality of rows of vacuum holes 24, each row having a plurality of vacuum holes 24, although more or less than those configurations or patterns shown can be used.

In operation, two webs of ear material 16 are carried by the anvil 114. One web of ear material 16 is located on each vacuum portion 116. A single ear 12 is cut from the ear web 16 when the rotary knife 18 engages the anvil roll 114 at the anvil pocket 122. Immediately after a single ear 12 is cut from the ear web 16, the single ear 12 is located on the ear retaining portion 124, particularly the tab portion 12a of the ear 12 as shown in FIG. 2. At this point the vacuum in the ear retaining portion 124 has been engaged to secure the single ear 12 to the anvil roll 114. As the anvil roll 114 rotates the vacuum is released at a predetermined location so that the single ear 12 can be applied to the diaper web 10. Because this configuration has two vacuum portions 116, a pair of two ears 12 is cut each time the rotary knife 18 engages the anvil roll 114. This allows for two pair of ears 12 to be cut with each revolution of the anvil roll 114. Shown in dotted line in FIG. 3 is a vacuum slot 128, described below.

Figure 4:
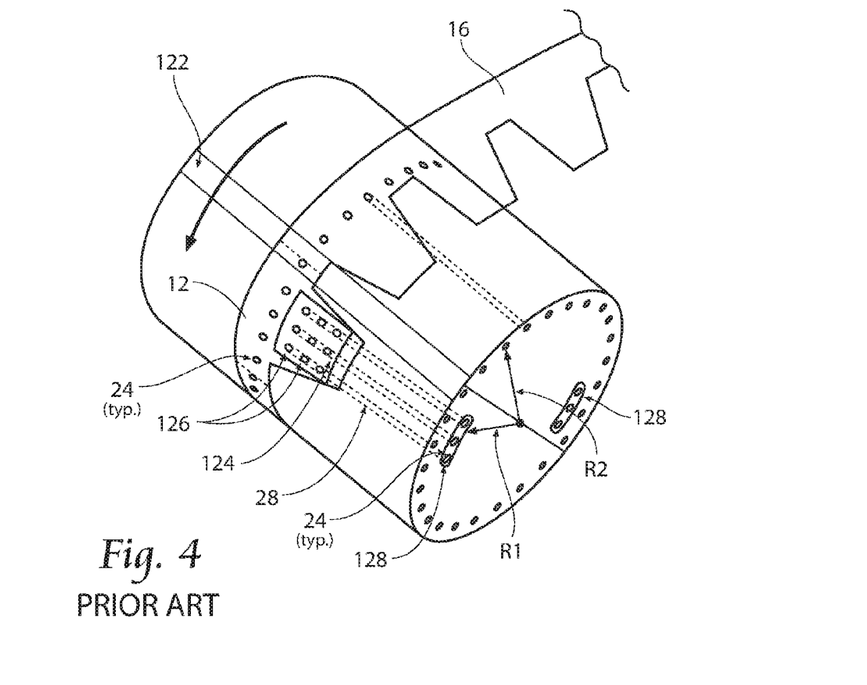
FIG. 4 is a perspective view of a prior art anvil roll.

Referring now to FIG. 4, a perspective view of the anvil 114 is shown. The anvil 114 will be described in relation to its endface and its outer surface, the outer surface that surface shown on FIG. 3 and the endface the two ends of the anvil 114.

The vacuum slot 128 contains a plurality of vacuum holes 24 that allow commutation of the vacuum to the entire ear vacuum hole pattern 126, allowing the pattern 126 to be activated simultaneously, as opposed to each of the rows that comprise the vacuum of vacuum holes 24 being enabled one at a time. The vacuum pattern 126 is activated utilizing drilled ports 28 that communicate the vacuum from the slot 128 to the individual holes 24 of the pattern 126. It should be noted that the pattern 126 can also be provided with a depressed slot configuration so that it too is all simultaneously enabled with vacuum.

The remaining vacuum holes 24 provided on the anvil roll 114 are enabled sequentially, by known vacuum commutation method utilizing cross drilled ports 28.

The vacuum slot 128 is provided at a first radius R1 on the anvil roll 114, the remaining vacuum holes provided at a different R2, The differing radii R1 and R2 allow two vacuum manifolds (not shown) to communicate each at a different radius, R1 or R2, thus selectively applying vacuum to the anvil.

Figure 5:
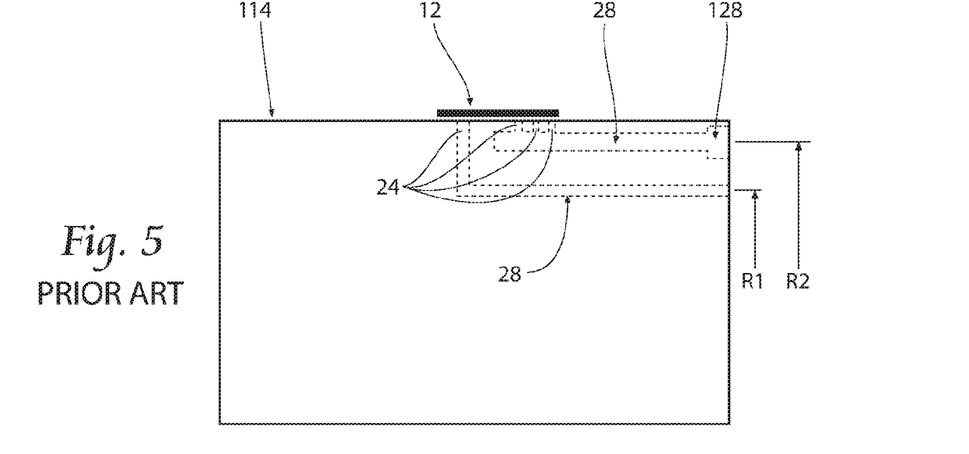
FIG. 5 is a cross sectional view of the prior art anvil roll.

Referring now to FIG. 5, a cross sectional view of the anvil roll 114 of the prior art is shown. In this embodiment, the slot 128 has been placed at R2. It is appreciated that the slot 128 communicating with the pattern 126 can be placed at either R1 or R2, and the remaining vacuum holes 24 communicating with drilled ports 28 can be interchanged at either R1 or R2. For machining purposes, it is likely preferable to place the slot 128 communicating with the pattern at R2 for simplicity in machining.

Figure 6:
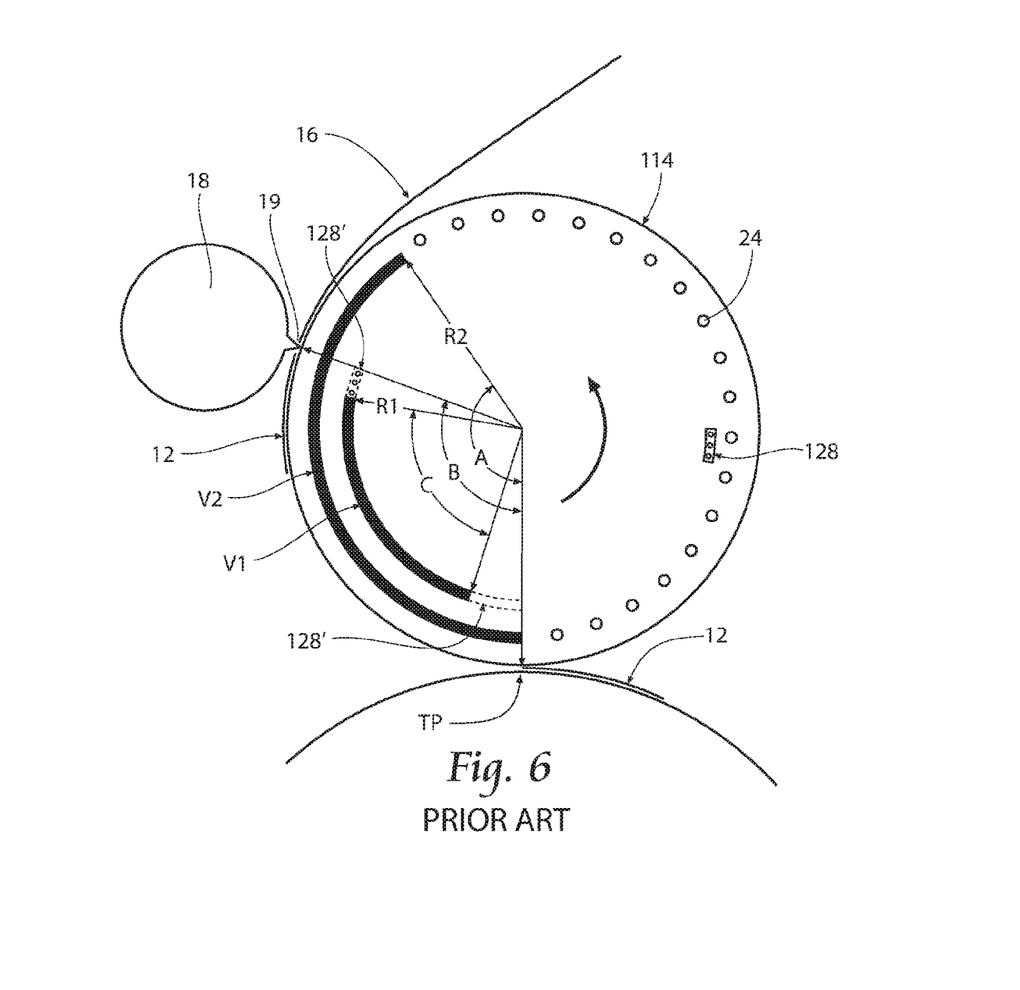
FIG. 6 is a side view of the prior art anvil roll, showing an endface of the anvil, and a vacuum manifold pattern applied to vacuum holes disposed on the endface of the anvil.

Referring now to FIG. 6, a side view of the anvil roll 114 is shown, showing the endface of the anvil, or the circular portion of the cylindrical body 114. The ear web 16 is shown infeeding to the anvil 114, where it is then cut with the rotary knife 18. It is desired to apply the vacuum to the pattern 126 simultaneously with the knife cut.

The range of vacuum application may be provided for with a manifold (not shown) that continuously applies vacuum to vacuum patterns V1 and V2. Vacuum pattern V1 is at R1, Vacuum pattern V2 is at R2. Vacuum pattern V1 applies vacuum to the slot 128 each time the slot 128 rotates through the vacuum pattern V1 provided on the manifold. When the slot 128 is in communication with V1, vacuum is applied to vacuum holes 24 associated in the slot 128 on the endface of the anvil for commutation to the pattern 126 on the outer surface of the anvil 114. When the slot 128 is not in communication with V1, the vacuum to the pattern 126 is turned off.

Vacuum pattern V2 is applied to the vacuum holes 24 disposed on the endface of the anvil 114 and the associated circumferential ribbon vacuum hole pattern on the outer surface of the anvil 114 throughout V2. As each successive vacuum hole 24 rotates through V2, the vacuum is on. As each successive vacuum hole 24 leaves V2, its vacuum is turned off.

From the center of the endface, a radius extending to the contact point of the knife 18 with the anvil roll 114 can be extended, and as the anvil roll rotates through angle B as shown, the rotation of the ear 12 will be from the knife point to the transfer point TP. It is throughout this angle B that vacuum is desired across the pattern 126 and onto the ear 12. To accomplish this, a smaller angle C has vacuum applied to it. The angle C can be expressed mathematically as the angle B minus twice the width 128' of the slot 128. This is because pattern 126 is placed in communication with the slot 128, the slot 128 communicates vacuum simultaneously to the pattern 126. Therefore, the leading edge of the ear 12 and the trailing edge of the ear 12 will receive vacuum at the same time. Therefore, the user must allow the leading edge of the ear 12 to pass by the knife 18 the desired length of the ear 12 prior to engaging the vacuum onto the ear 12. Similarly, prior to arriving at the transfer point TP, the vacuum will have to be released on both the leading and trailing edges of the ear 12 simultaneously, allowing the ear 12 to continue on its downstream path.

An angle A, larger than angle B, is provided to define V2, as it is desired to draw the web 16 into contact with the anvil both prior to and during cutting by the knife 18.

Many of the same transport functions are accomplished by the present invention using conveyance techniques accomplished without vacuum or with minimal assisted vacuum. Both flat and rotational conveyance are contemplated in the description below.

Figure 7:
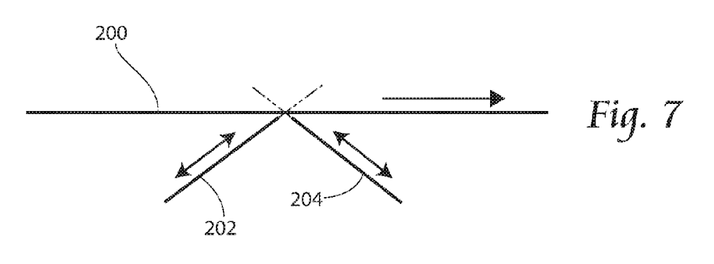
FIG. 7 is a side view of a conveyor belt with forward and rearward facing retractable spikes.

Referring now to FIG. 7, retractable spikes 202 and 204 above a belt can grip in both directions (202 slanted to the right, machine direction, forward; and 204 slanted to the left, reverse) and retract when needed, through a belt 200 or cylinder wall.

Figure 8:
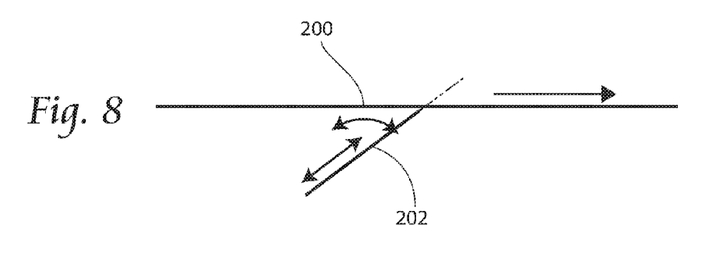
FIG. 8 is a side view of a conveyor belt with forward facing retractable spikes.

Referring now to FIG. 8, an alternate embodiment is shown with unidirectional spikes 202, slanted to the right, machine direction, forward.

Figure 15:
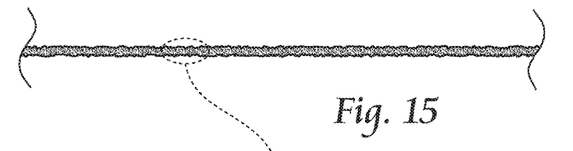
FIG. 15 is a side elevation view of a non-woven web material.
Figure 15A:
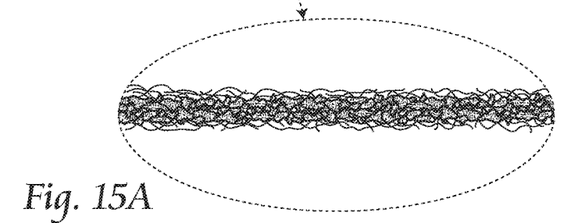
FIG. 15A is a close-up view of the nonwoven material of FIG. 15.
Figure 16:
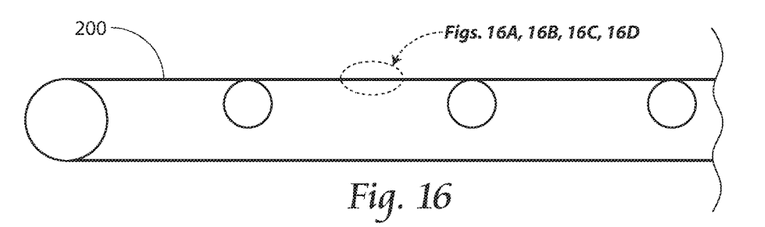
FIG. 16 is a side elevation view of a material conveyor belt.
Figure 16A:
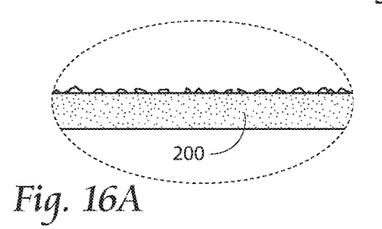
FIGS. 16A-16D are close-up side elevation views of optional coatings applied to the belt of FIG. 16.
Figure 16B:
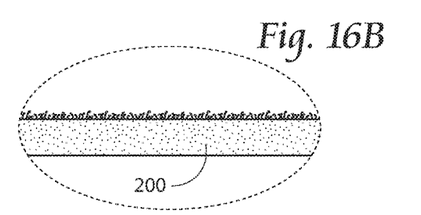
Figure 16C:
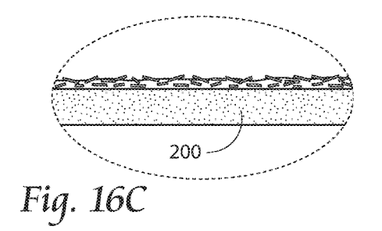
Figure 16D:
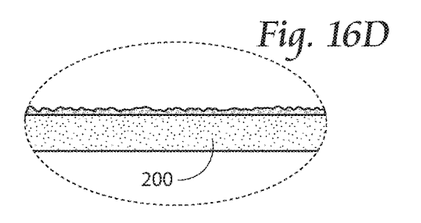

In lieu or in addition to spikes, a mechanical grip can be accomplished by using either a hook fastener (such as the hook component of a hook and loop fastening system) (see FIG. 16B) or rough sandpaper (see FIG. 16A), which both can grip well and release provided the nonwoven is pulled upward when leaving these surfaces. Additionally, other surfaces such as thermal spray applied texture, shot peening texture, knurling, and Electric discharge machining (EDM) surface features can also provide a mechanical grip of sufficient strength. As can be seen in FIGS. 15, a nonwoven material generally has a fuzzy finish, which may be frictionally engaged with such exemplary surfaces as metallic-fiber impregnated material (see FIG. 16C) or elastomeric resin coating (see FIG. 16D).

The spikes 202 and 204 of FIGS. 7 and 8 could be retracted in a number of ways. When it is desired to transfer the web or film to another belt or roller, the next processing step can be placed above the plane of transport. Considering the forward spike 202 example of FIG. 8, the nonwoven would simply lift off the spike if the nonwoven is lifted in an upward direction or takes place at a faster speed than the current step. Alternatively, the bottom end of the spikes 202 and 204 can be attached to another belt (not shown) travelling below the pictured belt. That lower belt can be made to drop down at the point in the process where it is desired to pull the spikes out of the web. The spikes 202 and 204 can be made to decelerate with respect to the upper belt and that forces the forward facing spikes 202 to drop down or out of the nonwoven. Still alternatively, the spiked surface could be mounted on individual segments like tractor treads. This would allow modular replacements if the material becomes worn or damaged. It would also allow fixture of a rough surface (such as hook material as in a hook and loop material) to a belt and avoid delamination from the upper material having a different curvature than the lower belt when it goes up or down in the described process.

The same principles described above can be applied to cylinders, such as the cylinder of FIG. 1. In such an arrangement, an inner cylinder carries the spikes 202 or 204 protruding from it and through an outer shell with holes or slots in it. The angle of the spikes 202 or 204 can be adjusted by changing the relative speed of the inner and outer cylinders. The cylinder could be used for hold and transfer operations by having the inner cylinder comprising several portions of cylinders (i.e. arcs) that can each move independently and allow one portion of the outer cylinder to be gripping the nonwoven while another portion of that cylinder is releasing the nonwoven.

Figure 9:
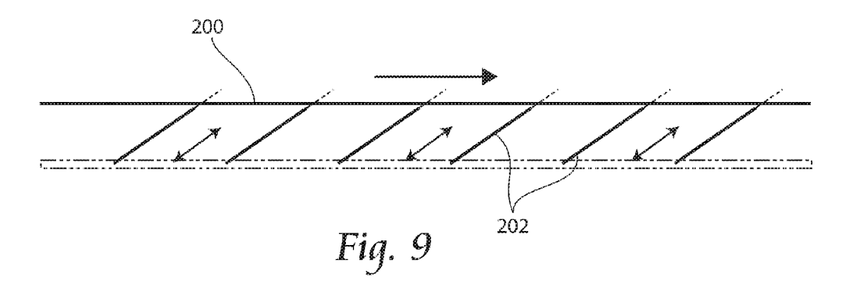
FIG. 9 is a side view of a Venturi effect enabled belt, with downward blades carried by a conveyor.
Figure 10:
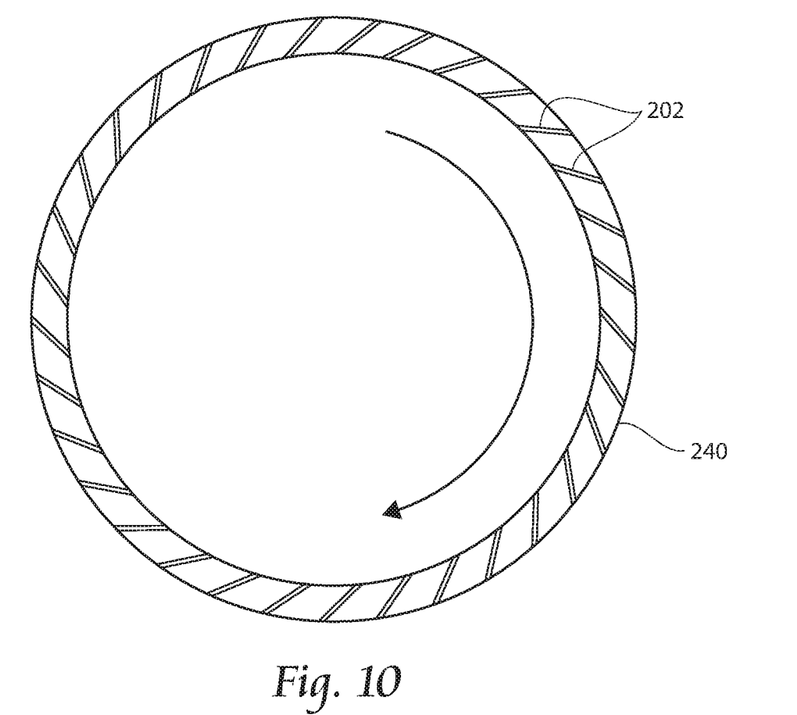
FIG. 10 is a cross-sectional side view of a drum with vanes.
Figure 11:
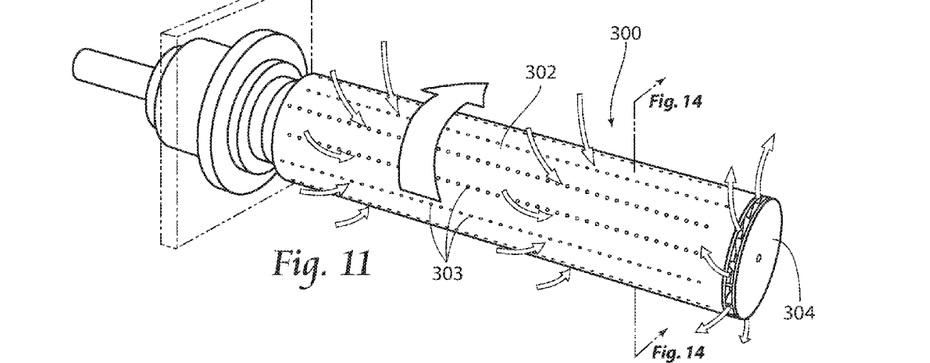
FIG. 11 is a perspective view of an embodiment of a conveyor drum capable of a passive Venturi draw.
Figure 12:
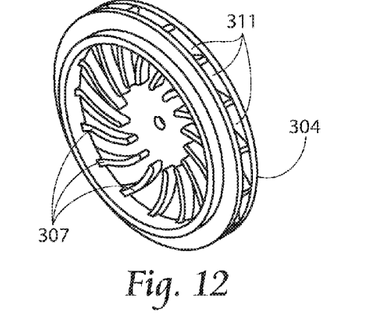
FIG. 12 is a perspective view of an embodiment of a fan plate according to the present invention.
Figure 13:
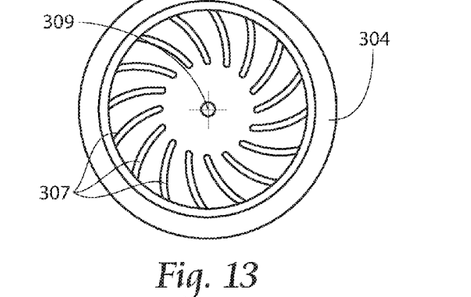
FIG. 13 is an elevation view of the plate of FIG. 12.
Figure 14:
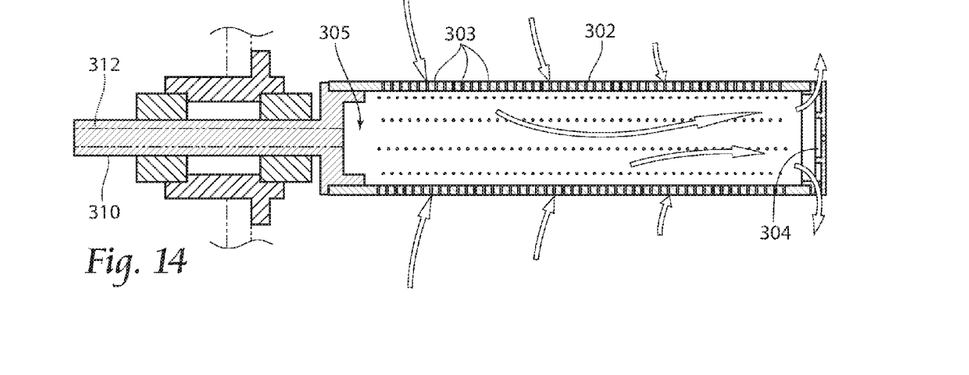
FIG. 14 is a cross-sectional view taken along line 14-14 of FIG. 11.

As applied to a configured belt, holes in the surface for vacuum and the forward flow would take with downward facing blades that drag the air forward. For example, downward facing blades 202 could be applied to a belt 200 as shown in FIG. 9. Alternatively, these blades could be made into a chevron shape so that they face downward (not shown), but also have the edges extending ahead of the chevrons apex. The chevron sides can block air from entering laterally, while the space below the belt can be open. The only place to draw replenishing air would be through the vacuum holes in the belt. At sections where it is desired to release the nonwoven, air can be blown vertically from below the belt at those fixed positions to erase any Venturi effect. The same concept can be applied to cylinders with and open center so that the air flow generated by those blades driving the air downward, can be channeled out the sides of the rotating cylinder. To use this technique in a cut and space execution, two outer cylinders within which this bladed cylinder turns can be employed (not shown). The cylinder adjacent to the bladed cylinders can be fixed with holes drilled at locations where holding is needed, and no holes in sections where transfer is needed. An exterior cylinder is drilled with holes provided, and turning at the speed needed to convey the web, Referring now to FIG. 11, a cross-sectional side view of a drum 240 with vanes 202 is show. This cylindrical drum 240 is a bladed cylinder revolving in the direction shown at a speed desired to convey the nonwoven. The vanes 202 have the effect of creating a vacuum by allowing air outside the drum 240 to be drawn into the drum 240 through vanes 202 in vane 202 voids not covered by non-woven and thereby create negative pressure within the drum 240 to voids covered by non-woven. Fixed blowers within the cylinder (not shown) direct air outward through the revolving cylinder at the locations where a blow-off is desired. These chevron blades or vanes 240 can also comprise partial blades with segments missing where it is desired to direct the outward air flow so that blower tubes can be positioned very near the revolving inner surface of the cylinder 240. The concept of providing through vanes 202 would also work in a belt, flat or curved.

An alternate embodiment 300 is shown in FIGS. 11-14. In this embodiment, a conveying drum 302 has a plurality of holes 303 formed through its outer surface, which lead to an internal drum cavity 305. In conventional systems, a powered vacuum was coupled to such drum cavity 305 to draw air through the holes 303 at predetermined locations about the rotational path of the drum 302. In this embodiment 300, however, the air pressure within the cavity 305 is reduced not by an external powered vacuum, but by a fan plate 304 coupled to the non-drive end of the drum 302. The plate 304 has a plurality of vanes 307 extending outwardly from its axis of rotation 309, the vanes 307 terminating at open airflow ports 311 about the circumference of the plate 304. As the drum 302 is rotated, the vanes 307 draw ambient air from within the drum cavity 305 and force it out of the ports 311. In this fashion, the increased velocity of the moving air inside of the cavity 305 causes the pressure of such air to drop, thereby drawing air into the cavity 305 through the holes 303 from outside of the drum 302, thereby causing a passive Venturi draw to hold materials to the surface of the drum 302. While the drum may be driven by a drive shaft 310, an optional air passage 312, in communication with the drum cavity 305, may be provided through at least a portion of the drive shaft 312.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

We claim:
1. A system comprising:
a conveyor comprising a material surface for moving a web material along a transfer path;
a plurality of holes formed through the material surface, the plurality of holes in fluid communication with a cavity;
a fan plate for drawing air out of the cavity to cause air to flow through the holes and into the cavity, the fan plate being oriented substantially perpendicular to the conveyor;
wherein the fan plate is driven by the conveyor.

2. The system of claim 1, wherein the fan plate comprises an inner surface and an outer surface, and wherein a plurality of vanes and associated airflow ports are situated between the inner surface and the outer surface.

3. The system of claim 2, wherein the outer surface is substantially closed.

4. The system of claim 2, wherein the fan plate has an axis of rotation and the vanes extend outwardly from the axis.

5. The system of claim 2, wherein the airflow ports are located around the circumference of the fan plate.

6. The system of claim 1, further comprising a drive system located on a first end of the conveyor opposite a second end of the conveyor, wherein the fan plate is located on the second end of the conveyor.

7. The system of claim 6, further comprising a drive shaft in the drive system, wherein an air passage extends through the drive shaft.

* * * * *